(12) United States Patent
Seemann

(10) Patent No.: US 6,918,912 B2
(45) Date of Patent: Jul. 19, 2005

(54) CONDYLUS SCREW

(75) Inventor: Michael Seemann, Altenholz (DE)

(73) Assignee: Stryker Trauma GmbH (DE)

( * ) Notice: Subject to any disclaimer, the term of this patent is extended or adjusted under 35 U.S.C. 154(b) by 128 days.

(21) Appl. No.: 09/934,630

(22) Filed: Aug. 22, 2001

(65) Prior Publication Data
US 2002/0055743 A1 May 9, 2002

(30) Foreign Application Priority Data

Aug. 24, 2000 (DE) ..................................... 200 14 648 U

(51) Int. Cl.⁷ ............................................. A61B 17/52
(52) U.S. Cl. ......................................... 606/73; 606/72
(58) Field of Search ............................. 606/73, 62, 63, 606/60, 72, 71, 70; 411/338, 371, 342, 907

(56) References Cited

U.S. PATENT DOCUMENTS

| | | | |
|---|---|---|---|
| 1,325,285 A | | 9/1919 | Landgraf |
| 1,409,157 A | | 3/1922 | Dodds |
| 1,616,232 A | * | 2/1927 | Roberts et al. ............. 411/338 |
| 2,511,051 A | * | 6/1950 | Dzus ........................... 606/73 |
| 4,615,655 A | | 10/1986 | Dixon |
| 5,056,208 A | | 10/1991 | Stafford |
| 5,108,399 A | | 4/1992 | Eitenmuller et al. |
| 5,269,784 A | * | 12/1993 | Mast ............................ 606/69 |
| 5,409,486 A | | 4/1995 | Reese |
| 5,542,777 A | * | 8/1996 | Johnson ...................... 403/389 |
| 5,607,426 A | * | 3/1997 | Ralph et al. ................. 606/61 |
| 5,738,685 A | | 4/1998 | Halm et al. |
| 5,797,912 A | | 8/1998 | Runciman et al. |
| 5,975,821 A | | 11/1999 | Kue |
| 5,976,141 A | | 11/1999 | Haag et al. |
| 6,010,505 A | | 1/2000 | Asche et al. ................. 606/62 |
| 6,063,090 A | * | 5/2000 | Schlapfer .................... 606/61 |
| 6,241,731 B1 | | 6/2001 | Fiz |
| 6,302,887 B1 | * | 10/2001 | Spranza et al. .............. 606/73 |
| 6,331,179 B1 | * | 12/2001 | Freid et al. .................. 606/61 |

FOREIGN PATENT DOCUMENTS

| | | | |
|---|---|---|---|
| AT | 386 118 | 7/1988 | |
| DE | 38 31 657 A1 | 3/1990 | |
| DE | 39 42 326 | 6/1991 | |
| DE | 94 08 668 | 9/1995 | |
| DE | 295 21 456 | 6/1997 | |
| DE | 296 15 482 | 2/1998 | |
| EP | 0 360 139 | 3/1990 | |
| EP | 0 685 206 B1 | 12/1995 | |
| EP | 0 997 107 A2 | 5/2000 | |
| FR | 2 555 645 | 5/1985 | |
| FR | 2 642 643 | 8/1990 | |
| FR | 2 659 546 | 9/1991 | |
| FR | 2 729 074 | 7/1996 | |
| FR | 2 822 052 A1 | 3/2001 | |
| FR | 2822052 | * 9/2002 | ............. 606/61 |
| GB | 2 324 964 | 11/1998 | |
| JP | 2-121652 | 5/1990 | |
| JP | 10 14936 | 1/1998 | |

* cited by examiner

Primary Examiner—Pedro Philogene
(74) Attorney, Agent, or Firm—Lerner, David, Littenberg, Krumholz & Mentlik, LLP

(57) ABSTRACT

An osteosynthetic device, particularly a condylus screw, which is composed of a female-type part and a shank part which each have a flanged portion. At least one flanged portions is a separate part and is formed as a ring-shaped bearing component which forms a bearing seat for a spherically-shaped end portion of the female-type part and/ or the shank part and wherein the bearing is movably supported on the female-type and/or the shank part.

29 Claims, 2 Drawing Sheets

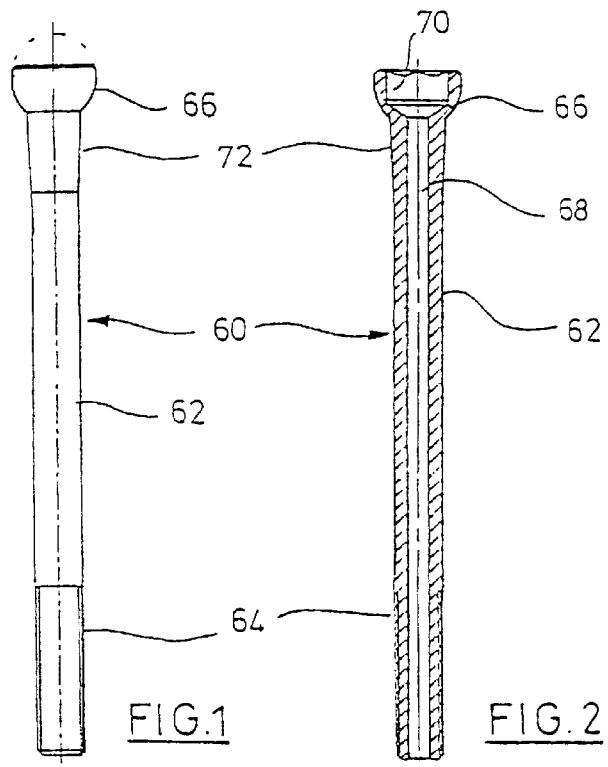
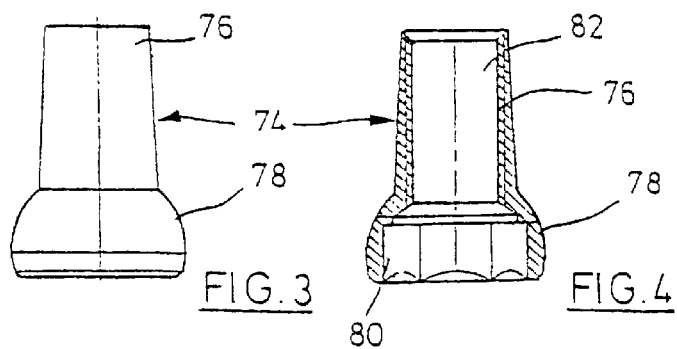
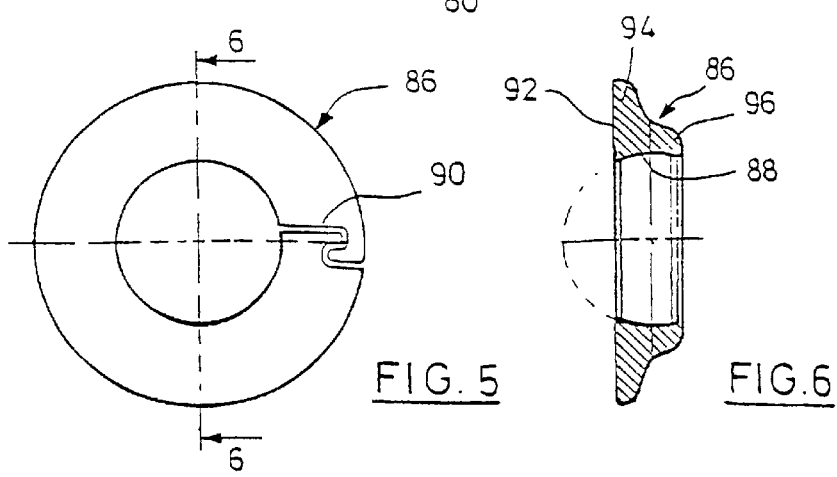

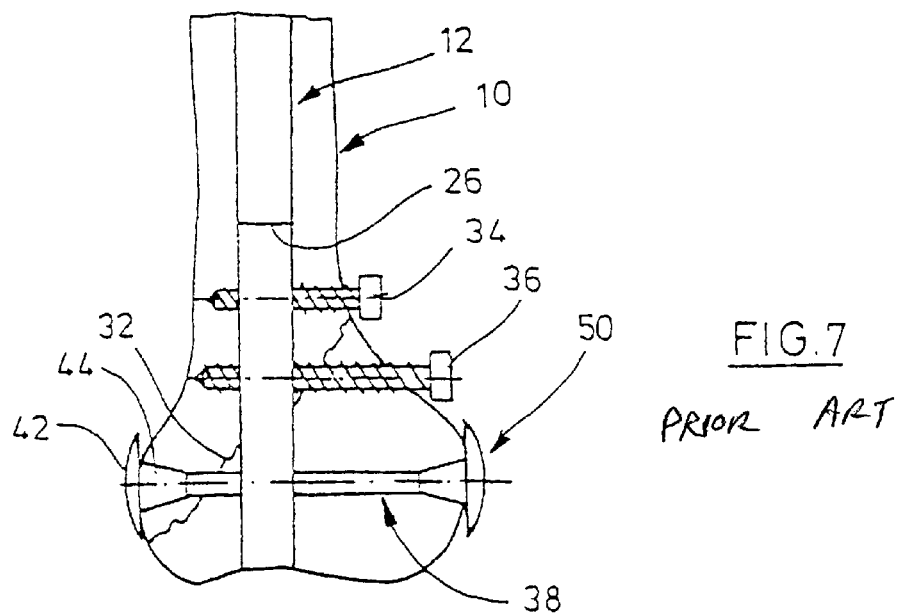
FIG. 7 PRIOR ART
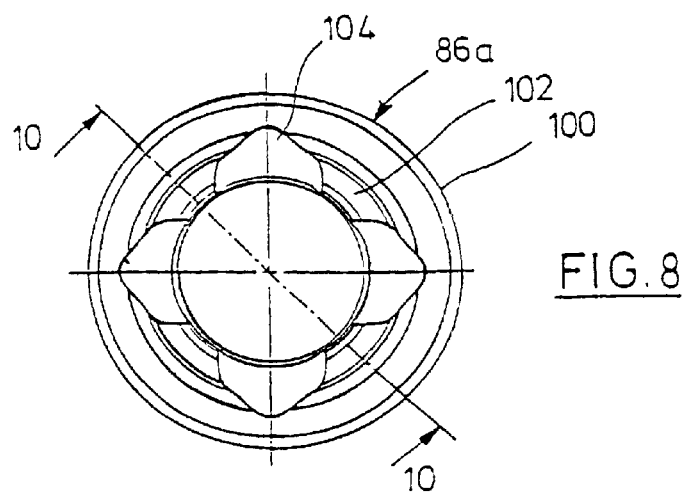
FIG. 8
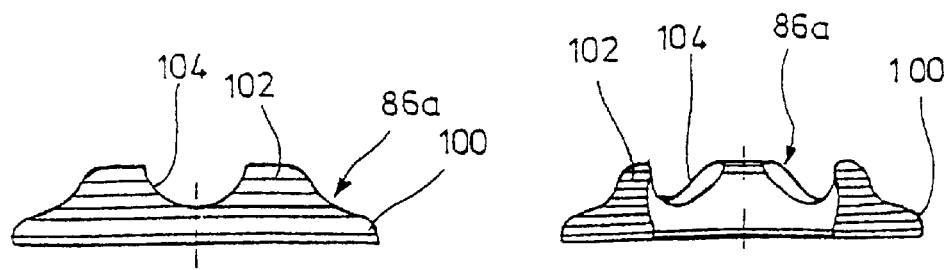
FIG. 9
FIG. 10

CONDYLUS SCREW

BACKGROUND OF THE INVENTION

The invention relates to an osteosynthetic condylus screw generally for use with a bone nail. In certain types of fractures the condylus screw can be used without the bone nail.

A supracondylar or retrograde bone nail is disclosed in U.S. Pat. No. 6,010,505. It has an elongate shank which is shaped relatively short as compared to other femoral nails and is driven in through a bore which distally opens out between the condyli and, for the rest, follows the bone channel. To take good care of a fracture in the condylus region, a so-called condylus screw is provided which can be passed through a transverse bore of the bone nail. The condylus screw has a female-type portion and a shank portion which are screwed together. At each end, the portions have a flange-like extension which bears on the bone side which faces it. Such a screw makes it easy to efficiently compress the bone fragments and retain them on the nail. The latter normally is designed as a so-called locking nail.

The extent to which the flanged-like extension bears on the bone depends on the position exhibited by the ends of the condylus screw, and the outer contour of the bone. It might readily happen that only small surface regions will bear thereon, thus producing an undesirably high contact pressure.

SUMMARY OF THE INVENTION

It is the object of the invention to provide an osteosynthetic device which avoids the disadvantage described and which allows optimum adaptation to the bone.

In the screw of the present invention, at least one flanged portion is shaped as a separate part and is in the form of a ring-shaped bearing component which is movably supported on a spherically-shaped end portion of the female-type part or the shank part of the condylus screw. The movable, preferably pivotable, bearing of the flange-like portion provides for movability in all directions so that optimum adaptation is made to the prevailing surface conditions and, thus, minimal contact pressure is applied to the bone surfaces.

Various constructional measures are possible to join the flange-like portion to the ball-shaped end portion. According to the invention, one design feature provides that the bearing part be shaped so as to allow it to snap onto the ball-shaped end portion. However, care has to be taken that the snap-on connection be designed so as to prevent it from inadvertently getting separated while or after the screw is mounted. In particular, the two elements must not snap out in the direction of pull.

According to the invention, a particularly simple constructional version consists in that some sort of bearing socket is provided which has a slot, which permits resiliently widening the bearing socket. However, there is possibly a danger here that a tensile load also effects widening. Therefore, another aspect of the invention provides that the slot be shaped in such a way that the ends of the bearing socket which face the slot can be moved away from each other only to a limited degree. Such a slot, for example, may be of an S or Z shape. As soon as the motion to move apart the ends of the ring-shaped bearing socket exceeds a preset extent portions of the slot will bear on the slot and prevent any widening.

As in the case which is known from the prior art, the side of the bearing part, which faces the bone, can be of a planar shape. The opposite side preferably is of a rounded contour to prevent lesions to the tissue.

An alternative option also consists in the bearing socket or bearing ring not being slotted, but providing axially parallel webs which are conformed to the ring-shaped bearing part in their circumferential spacing and define some part of the bearing socket-like recess. The raised webs grip around the ball-shaped end portion and land in place in a slightly springable way while the end portion is being inserted. After being mounted, the webs prevent the end portion from getting out of the bearing ring.

The inventive screw or the inventive osteosynthetic device, for example, may be used with a supracondylar nail, but also with any other locking nail. However, it is also possible to use the osteosynthetic device herein with no bone nail if there is an appropriate attendance situation, i.e., in an appropriate fracture.

The invention will now be explained in more detail with reference to an embodiment shown in the drawings.

BRIEF DESCRIPTION OF THE DRAWINGS

FIG. 1 shows a side view of a shank portion of a condylus screw according to the invention;

FIG. 2 shows a longitudinal section through the illustration shown in FIG. 1;

FIG. 3 shows a side view of a female-type part of a condylus screw according to the invention;

FIG. 4 shows a section through the female-type part of FIG. 3;

FIG. 5 shows a plan view of the bearing socket for the condylus screw according to the invention;

FIG. 6 shows a section through the illustration of FIG. 5 taken along lines 6—6;

FIG. 7 shows a section through the distal femur part with a supracondylar nail and a condylus screw according to the state of the art;

FIG. 8 shows a plan view of a bearing part of another embodiment of the invention;

FIG. 9 shows a side view of the bearing part of FIG. 8; and

FIG. 10 shows a section through the bearing part of FIG. 8 taken along lines 10—10.

DESCRIPTION OF THE PREFERRED EMBODIMENTS

Initially, it should be noted that the drawings are not to scale.

Referring to FIG. 7, the distal region of a femur 10 is shown which receives a bone nail 12. It is inserted through a bore which is subcondularly made in a retrograde way. This is explained in detail in U.S. Pat. No. 6,010,505 the teachings of which are incorporated herein by reference.

The distal region of bone nail 12 is provided with three transverse bores. FIG. 7, the state of the art, further makes it evident that the condylus region of the femur is damaged by an obliquely extending fracture having a fracture line 32. Two bone screws 34, 36 are passed through two of the three transversal bores and serve to anchor nail 12 in femur 10. A condylus screw 38, which is composed of a shank part 50 and a female-type part 42, is passed through the distal transverse bore. The two parts 42, 50 are screwed onto each other (with the thread not being shown). The female-type part 42 and the shank part 50 have flange-like heads which are followed by conical portions 44. A condylus screw 38 helps to accomplish a compression. The flange-like heads are rigidly connected to the parts associated therewith. The parts of the condylus screw shown in FIGS. 1 to 6 are of a similar structure, but are configured in a particular way. This will be described in greater detail below.

The shank part of the preferred condylus screw of the present invention is indicated by 60 and is shown in FIGS. 1 and 2. It has a smooth, cylindrical shank portion 62, a threaded end portion 64, and a ball-shaped or ball section-shaped head 66. Shank part 60 is axially traversed by a through bore or cannulation 68. There is a hexagonal socket 70 in the head 66 for engagement with a tool for rotating the shank. The shank part 60 has a conical portion 72 near the head 66.

A female-type part 74 is illustrated in FIGS. 3 and 4. In the preferred embodiment, it has a conical threaded portion 76 having a female-type thread and a ball-shaped or ball section-shaped head 78 with a hexagonal socket 80. Female-type part 74 also has a through axial bore 82. As can be seen the shank part 60 and female-type part 74 are shown at different scales because the female-type part is screwed onto threaded portion 64 when in use with the free end of the conical portion 76 being of a diameter which is equal to the diameter of smooth shank portion 62.

In the preferred embodiment, a bearing disc 86 the contour of which can be seen from FIGS. 5 and 6 is snapped onto the ball-shaped heads 66 and 78. The bearing disc or bearing cup 86 is circular at its circumference and has an inner globular or ball-shaped bearing portion 88. Its dimensions are such that the ball-shaped head 66 of shank part 60 or the ball-shaped head 78 of the female-type part 74 can be received in an approximately or close fitting relationship. This enables bearing disc 86 to pivot to any side on the head associated therewith. According to FIG. 7, it can be seen that this would allow the bearing disc 68 to optimally bear on the condylus portion of the femur 10.

As can be seen from FIG. 5 the bearing disc 86 has a through Z-shaped slot 90. This slot permits the bearing disc 86 to be snapped onto head 66 and 78 when the ends of the ring-shaped bearing disc 86 which face the slot are slightly moved apart. It is understood that the bearing disc 86 is made of an appropriate resilient material. It further can be seen that the shape which preferably is non-linear of the S or Z shaped slot 90 prevents the ends of bearing disk 86 from being moved apart by more than the width dimension of the slot 90. Hence, the female-type part or shank part may apply a pressure, which is not insignificant, to the bearing disk 86 during compression with the parts not being separated from each other.

It can be seen from FIG. 6 that the side of bearing disc 86 which faces the bone is planar as is shown at 92. The opposite side has a rounded contour which consists of a flanged portion 94 adjoining the surface 92 and a collar portion 96 towards the other side of the disc 86.

Two or three condylus screws may be used instead of one screw if this is made necessary by the fracture which is being treated.

Another embodiment of the bearing component 86a is shown in FIGS. 8 to 10 which has a ring-shaped portion 100 which is comparable to ring-shaped portion 94 of bearing component 86 of FIGS. 5 and 6. Four webs 102 are formed out of ring-shaped portion 100 which extend away from the ring-shaped portion 100 in a nearly axially parallel relationship and are disposed at spacings of approximately 90°. Rounded depressions 104 are formed between them. The depressions are semi-circular in the side view (FIG. 9). The projections or webs, 102 along with ring-shaped portion 100, define a bearing socket 88a. Socket 88a is interrupted by depressions 104 in the area of webs 102. A ball-shaped end portion such as end portion 66 of FIGS. 1 to 4 may be inserted into the bearing socket via the region of webs 102. This causes webs 102 to be resiliently deformed slightly radially towards the outside and, subsequently, will be snapped over the final portion so that the bearing component 86a is captively secured on the end portion. For the rest, the function of the bearing element 86a fully corresponds to that of bearing element 86.

The screw illustrated in FIGS. 1 through 6 and 8 through 10 is adapted to be used to attend the various cases of bones fractures, even with no bone nail as is shown in FIG. 7, for example. If it is employed in the situation shown in FIG. 7 the screw 38 would be replaced with the screw of the present invention. Screws 34, 36 of FIG. 7 can also be replaced with the screw of the present invention. The heads of the screw shown in FIGS. 5, 6, and 8 to 10 allow the screws to optimally bear on the bones because they are pivotable. This is not ensured, for example, by the heads of screws 34, 36 in FIG. 7.

What is claimed is:

1. An osteosynthetic device, comprising a female-type part and a shank part which have a flanged portion each, at least one flanged portion is a separate part and is formed as a ring-shaped bearing component having a continuous outer circumference having a bone contacting surface on a first side and an opposite second side which forms a ball-shaped bearing seat for receiving a ball-shaped end portion of at least one of the female-type part or the shank part, and being movably supported therein wherein the ball-shaped seat of the bearing component has a plurality of smaller webs facing outwardly from said second side, said webs having inner surfaces forming a smaller relaxed diameter than the diameter of the head so as to allow the bearing component to be snapped onto the ball-shaped end portion on movement of said ball-shaped end portion in the direction from said second side to said first side.

2. The osteosynthetic device according to claim 1, wherein sides of the bearing component which face each other are of a planar shape.

3. The osteosynthetic device according to claim 1, wherein a side of the bearing component which faces outwardly has a rounded contour.

4. The osteosynthetic device according to claim 1, wherein the shank part and the female-type part each have a through axial bore.

5. The osteosynthetic device as set forth in claim 1 wherein said ball-shaped seat has four webs.

6. The osteosynthetic device as set forth in claim 5 wherein said webs are spaced at approximately 90°.

7. The osteosynthetic aid as set forth in claim 6 wherein the webs are separated by semi-circular depressions.

8. A condylus screw comprising:
a first part having a head portion and a shank portion extending along an axis;
a second part having a head portion and a portion for coupling to said shank; and
a bearing component for rotatably engaging the head portion of at least one of said first and second parts for pivotal movement with respect to said axis, wherein said bearing component is in the form of a disc having a central bore for receiving said shank of said first part, a bone contacting surface, an outwardly facing surface opposite said bone contacting surface and wherein the disc has a non-linear slot extending from said central bore to an outer circumference thereof from said outer surface to said bone contacting surface.

9. The condylus screw as set forth in claim 8, wherein at least one of said first and second parts have a head with spherical bearing surfaces.

10. The condylus screw as set forth in claim 9, wherein said bearing component has a spherical surface for engaging said spherical surface of the head of said at least one part.

11. The condylus screw as set forth in claim 10, wherein said shank of said first part has a threaded portion for engaging a threaded portion of said second part for coupling said first and second parts.

12. The condylus screw as set forth in claim 8, wherein said bearing component after engagement with at least one of said first and second parts has a planar bone contacting surface facing the other of said first or second parts.

13. The condylus screw as set forth in claim 8 wherein the slot is S or Z-shaped.

14. A condylus screw comprising a first part and a second part, said first part having a head and a shank extending along an axis, said shank of said first part for extending into said condylus in a generally medial-lateral direction, said second part having a head and a portion for engaging said shank of said first part and at least one of the heads of said first and second parts having a bearing portion pivotable in a direction transverse to said axis wherein said pivotable bearing portion is a separate bearing component wherein said bearing component is in the form of a disc having a central bore for receiving said shank of said first part, a bone contacting surface, an outwardly facing surface opposite said bone contacting surface wherein the disc has a non-linear slot extending from said central bore to an outer circumference thereof from said outer surface to said bone contacting surface.

15. The condylus screw as set forth in claim 14, wherein at least one of said first and second parts have heads with spherical bearing surfaces.

16. The condylus screw as set forth in claim 15, wherein said bearing component has a spherical surface for engaging said spherical surface of the head.

17. The condylus screw as set forth in claim 16, wherein said shank of said first part has a threaded portion for engaging a threaded portion of said second part for coupling said first and second parts.

18. The condylus screw as set forth in claim 14, wherein said bearing component after engagement with at least one of said first and second parts has a planar surface facing the other of said first or second parts.

19. The condylus screw as set forth in claim 14 wherein the slot is S or Z-shaped.

20. A bone fastener comprising a head portion and a bone engaging shank extending from the head and a flanged bearing component having a bore for receiving the shank surrounded by a bearing seat for receiving the head portion on one side thereof and having a bone contacting bearing surface on the other side thereof, the bearing component having an integral means thereon for allowing limited radial expansion of the bearing component seat to resiliently receive said head while maintaining said bore diameter less than said head diameter said limited radial expansion caused by interaction between the fastener head and the bearing component seat on movement of the head towards the bone contacting surface of the bearing component as said shank engages said bone.

21. The bone fastener as set forth in claim 20 wherein the bearing component is split by a slot which is shaped in such a way that ends of the bearing seat which face the slot can be moved away from each other only to a limited degree.

22. The bone fastener as set forth in claim 21 wherein said slot is Z or S-shaped.

23. The bone fastener as set forth in claim 20 wherein the bone contacting surface sides of the bearing component is of a planar shape.

24. The bone fastener as set forth in claim 20 wherein a side of the bearing component opposite the bone contacting surface and which faces outwardly has a rounded contour.

25. The bone fastener as set forth in claim 20 wherein the head and shank part have a through axial bore.

26. The osteosynthetic device according to claim 20 wherein the bearing component has a ball-shaped seat having a smaller relaxed diameter than the diameter of the head so as to allow the bearing component to be snapped onto the ball-shaped end portion and captively secured thereto.

27. The osteosynthetic plate as set forth in claim 20 wherein the bone contacting surface is planar.

28. An osteosynthetic device, particularly a condylus screw, comprising a female-type part and a shank part each of which have a flanged portion, at least one flanged portion is a separate part and is formed as a ring-shaped bearing component having a continuous outer circumference which includes a bearing seat for a ball-shaped end portion of at least one of the female-type part or the shank part, and being movably supported therein, wherein the bearing seat is a socket-shaped seat which is bordered by circumferentially spaced-apart, axially parallel projections, which limit an aperture for inserting the ball-shaped end portion and temporarily are radially deformed outwardly during the insertion procedure.

29. The osteosynthetic device according to claim 28, wherein rounded depressions are provided between the projections, which are formed in a ring-shaped portion of the ring-shaped bearing component approximately in parallel with an axis of the bearing component.

\* \* \* \* \*